United States Patent [19]

Holtkamp

[11] Plant 4,870

[45] Jul. 27, 1982

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 172,464

[22] Filed: Jul. 25, 1980

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet named Illinois, particularly characterized by its large pink, star-shaped flowers; strong, upright flower stems each carrying 7–10 flowers; heavy and prominent yellow pollen sacs; vigorous and uniform growth habit, producing a plant in full flower in 9–10 weeks.

1 Drawing Figure

The present invention comprises a new and distinct cultivar of African violet plant, botanically known as *Saintpaulia ionantha,* and hereinafter referred to by the cultivar name Illinois.

The new cultivar was referred to during the breeding and selection process by the designation E 148/1, and is a product of a planned breeding program. The basic objective of the breeding program was to create a new African violet cultivar having large, generally pink star-shaped flowers.

The new cultivar was originated from a cross made in a controlled breeding program in Isselburg, West Germany. The female, or seed parent was a cultivar designated b. 261/5 pink star. The male, or pollen parent was a cultivar designated b. 165/z pink.

The new cultivar Illinois was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and are retained through successive generations of asexual reproduction.

Illinois has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Illinois, which in combination distinguish this African violet as a new and distinct cultivar:

1. Large star-shaped flowers, which are long lasting and non-dropping.
2. Vigorous and uniform growth habit.
3. Strong and upright flower stems, 7–10 in number, each carrying 6–10 pink flowers.
4. Heavy and prominent yellow pollen sacs.
5. Attractive saleable plant with compact flowerhead within 10 weeks after potting.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Illinois.

Parentage:

*Male parent.*—b. 165/z pink.

*Female parent.*—b. 261/5 pink star.

Propagation: The new cultivar holds its distinguishing characteristics through successive propagations by leaf cuttings.

Plant: From 8 cm. to 10 cm. tall when grown in pots, and approximately 25–30 cm. in diameter when fully grown.

*Leaves:*

*General form.*—Round to heart-shaped.

*Diameter.*—Up to 60–70 mm.

*Texture.*—Soft and hairy.

*Aspect.*—Velvety, slightly shiny.

*Veins.*—Upperside visible; underside well-pronounced and shiny; on younger leaf underside brownish-purple and hairy.

*Color (upperside).*—HCC spinach green 0960.

*Color (underside).*—HCC 00862/1 but slightly lighter.

*Petiole.*—Young plant brownish green, hairy; old plant medium-green and hairy.

Flowers:

*Buds.*—Bell-shaped, 6–8 mm. just before opening, 6–10 buds per stem.

*Sepals.*—

*Color:* Brownish-green.

*Calyx:* Flat, funnel-shaped.

*Aspect:* Spear-shaped.

*Peduncle:* Short upright, brownish.

Individual flowers:

*Size.* —Between 40–55 mm.

*Color.*—

*Upperside:* Roseine purple 629/1.

*Underside:* Roseine purple 629/2. Center of older flowers magenta rose (027/1). Under cooler growing conditions, the color is more intensive.

*Borne.*—Flower stem carries 6–10 flowers on short strong peduncles; flowers occasionally display an additional small petal in the center.

*Shape.*—Star-shaped, slightly wavy; 5–7 petals, same size.

*Corolla.*—Full, positioned centrally above the leaves.

*Flowering time.*—6–7 weeks after potting, first flowers appear; 8–10 weeks to full flowering, saleable plant.

Reproductive organs:

*Anthers.*—5, composed of 2 cells with seed capsule pushed slightly through; color sulphur yellow/1.

*Filaments.*—3–4 mm. long, greenish yellow, partly pinkish.

*Styles.*—6 mm., light purple; base of ovary light green, very hairy.

*Pollen color.*—HCC Dresden yellow 64/3.

Roots: White when young and active; greenish brown when older; normally developed.

Disease resistance: Good as experienced to date.

General observations: Illinois is a very vigorous grower, coming to flower in approximately 6–8 weeks, and being in full flower in 9–10 weeks. The upright strong flower stems carry 6–10 and more attractive pink star flowers which are long-lasting and non-dropping. Older mature flower centers change to a more intensive pink color.

I claim:

1. A new and distinct cultivar of African violet known by the cultivar name Illinois, as described and illustrated, and particularly characterized by its large pink, star-shaped flowers; strong, upright flower stems each carrying 7–10 flowers; heavy and prominent yellow pollen sacs; vigorous and uniform growth habit, producing a plant in full flower in 9–10 weeks.

* * * * *

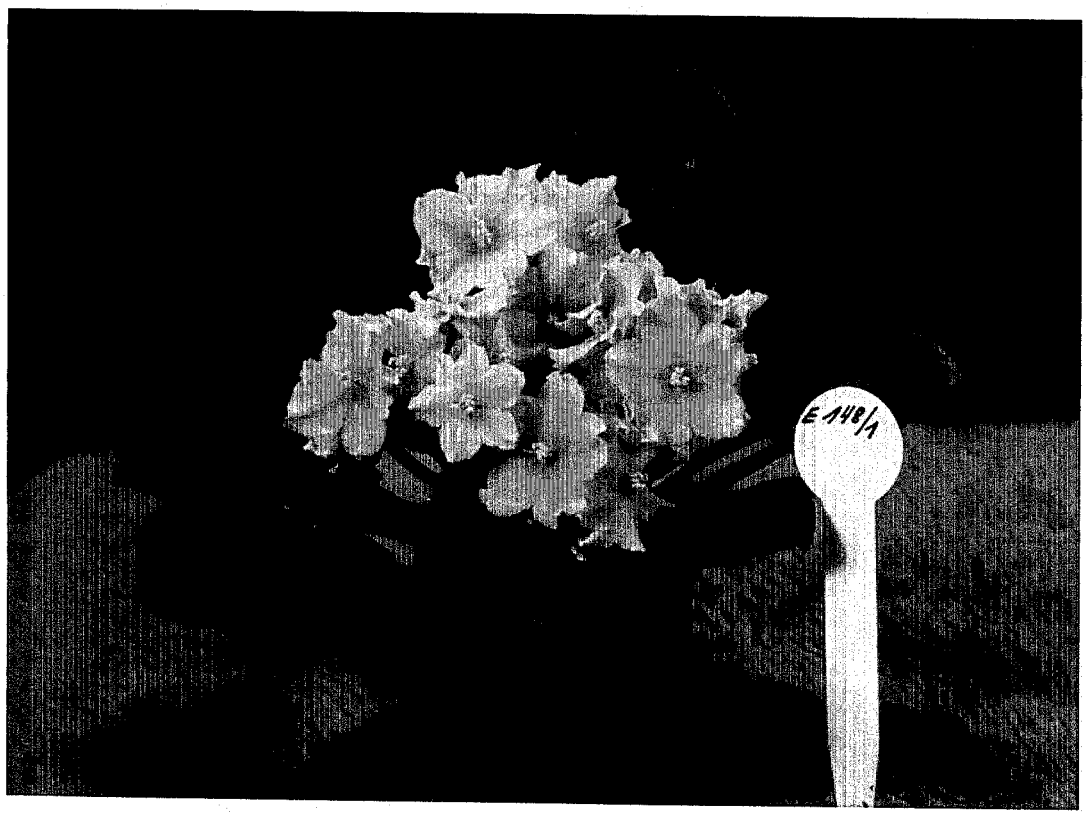
E 148/1